United States Patent
Szpirer et al.

(10) Patent No.: US 9,309,518 B2
(45) Date of Patent: Apr. 12, 2016

(54) REVERSIBLE, PARALLEL AND MULTITASK CLONING METHOD AND KIT

(71) Applicants: Cédric Szpirer, Fleurus (BE); Michel C. Milinkovitch, Jemeppe-sur-Sambre (BE); Philippe Gabant, Ottignies-Louvain-la-Neuve (BE)

(72) Inventors: Cédric Szpirer, Fleurus (BE); Michel C. Milinkovitch, Jemeppe-sur-Sambre (BE); Philippe Gabant, Ottignies-Louvain-la-Neuve (BE)

(73) Assignee: Universite Libre de Bruxelles, Brussels (BE)

( * ) Notice: Subject to any disclaimer, the term of this patent is extended or adjusted under 35 U.S.C. 154(b) by 604 days.

(21) Appl. No.: 13/660,907

(22) Filed: Oct. 25, 2012

(65) Prior Publication Data

US 2013/0115658 A1    May 9, 2013

Related U.S. Application Data

(63) Continuation-in-part of application No. 10/526,525, filed as application No. PCT/BE03/00147 on Sep. 3, 2003, now Pat. No. 8,318,497.

(60) Provisional application No. 60/408,482, filed on Sep. 3, 2002.

(51) Int. Cl.
| | |
|---|---|
| *C12N 15/66* | (2006.01) |
| *C12N 15/63* | (2006.01) |
| *C12N 15/10* | (2006.01) |
| *C12N 15/65* | (2006.01) |
| *C12N 15/70* | (2006.01) |

(52) U.S. Cl.
CPC ............... *C12N 15/63* (2013.01); *C12N 15/10* (2013.01); *C12N 15/65* (2013.01); *C12N 15/66* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 5,300,431 | A | 4/1994 | Pierce et al. |
| 5,631,153 | A | 5/1997 | Capecchi et al. |
| 5,670,370 | A | 9/1997 | Molin et al. |
| 5,855,732 | A | 1/1999 | Yoshida |
| 5,888,732 | A | 3/1999 | Hartley et al. |
| 5,910,438 | A | 6/1999 | Bernard et al. |
| 5,922,583 | A | 7/1999 | Morsey |
| 6,143,557 | A | 11/2000 | Hartley et al. |
| 6,171,861 | B1 | 1/2001 | Hartley et al. |
| 6,180,407 | B1 | 1/2001 | Bernard et al. |
| 6,270,969 | B1 | 8/2001 | Hartley et al. |
| 6,271,359 | B1 | 8/2001 | Norris et al. |
| 2004/0115811 | A1 | 6/2004 | Gabant |
| 2005/0130308 | A1 | 6/2005 | Bernard |
| 2005/0260585 | A1 | 11/2005 | Szpirer |

FOREIGN PATENT DOCUMENTS

| | | |
|---|---|---|
| DE | 10038573 | 2/2002 |
| WO | WO 94/03616 | 2/1994 |
| WO | WO 97/13401 | 4/1997 |
| WO | WO 97/14805 | 4/1997 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 A2 | 2/2002 |
| WO | WO 02/066657 | 8/2002 |

OTHER PUBLICATIONS (1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Aizenman, et al. (1996) An *Escherichia coli* chromosomal "addiction module" regulated by 3', 5'—bispyrophosphate: A modayk for programmed bacterial cell death. Proc. Natl. Acad. Sci. 93:6059-6063.
Backman, K. and H.W. Boyer (1983) "Tetracycline Resistance Determined by pBR322 is Mediated by one Polypeptide." Gene 26. pp. 197-203.
Bahassi, et al. (1995) F plasmid CcdB killer protein: *ccdB* gene mutants coding for non-cytotoxic proteins which retain their regulatory functions. Molecular Microbiology 15(6):1031-1037.
Baubonis, et al. (1993) Genomic Targeting with Purified Cre Recombinase. Nucleic Acids Research 21(9):2025-2029.
Baum, "Tn5401, a New Class II Transposable Element from Bacillus thuringiensis," Journal of Bacteriology, vol. 176. No. 10, May 1994, pp. 2835-2845.

(Continued)

*Primary Examiner* — Nancy T Vogel
(74) *Attorney, Agent, or Firm* — Knobbe Martens Olson & Bear LLP

(57) ABSTRACT

The present invention is related to integrated method and tools to construct recombinant DNA molecules (to be used as DNA vaccine or gene therapy) without requiring the use of antibiotic(s) resistance gene(s) and without requiring the addition of one or more antibiotic(s) to the culture medium of cells submitted to this recombinant DNA method. The present invention allows to obtain the selection of recombinant host cell(s) transformed by a (exogenous) nucleic acid sequence of interest (extra-chromosomal vector containing the insert) and simultaneously stabilization (stable inheritance) of this (exogenous) nucleic acid sequence of interest into the transformed host cell(s) descendants (maintenance of the nucleic acid sequence of interest in the host cells population).

12 Claims, 7 Drawing Sheets

(56) References Cited

OTHER PUBLICATIONS

Bech, et al., "Seaqence of the reLB transcription unit from *Escherichia coli* and Identification of the reLB gene," The EMBO Journal, vol. 4, No. 4, pp. 1059-1066, 1985.
Bernard (1996) Positive Selection of Recombinant DNA by CcdB. BioTechniques 21(2)320-323.
Bernard, et al. (1991) The 41 carboxy-terminal residues of the miniF plasmid CcdA protein are sufficient to antagonize the killer activity of the CcdB protein. Mol. Gen Genet 226:297-304.
Bernard, et al. (1992) Cell Killing by the F Plasmid CcdB protein involves poisoning of DNA-topoisomerase II complexes. J. Mol. Biol. 226:735-745.
Bernard, P., et al. (1994) Positive-Selection Vectors Using the F Plasmid ccdB Killer Gene. Gene 148, pp. 71-74.
Bex, et al. (1983) Mini-F encoded proteins: Identification of a new 10.5 kilodalton species. The EMBO Journal, 2(11):1853-1861.
Biswas, et al. (1993) High-Efficiency Gene Inactivation and Replacement System for Gram-Positive Bacteria. J. Bacteriology 175(11):3628-3635.
Bochner, et al. (1980) Positive Selection for Loss of Tetracycline Resistance. J. Bacteriology 143(2):923-933.
Boyd (1993) Turbo Cloning: A Fast, Efficient Method for Cloning PCR Products and Other Blunt-Ended DNA Fragments into Plasmids. Nucleic Acids Research 21(4):817-821.
Bravo, et al. (1988) Killing of *Escherichia coli* cells modulated by components of the stability system ParD of plasmid R1. Mol. Gen. Genet. 215:146-151.
Bubeck, et al. (1993) Rapid Cloning by Homologous Recombination in vivo. Nucleic Acids Research 21(15):3601-3602.
Bult, "Complete Genome Sequence of the Methanogenic Archaeon, Methanococcus Jannaschii," Science, vol. 273, Aug. 23, 1996, pp. 1058-1073.
Burns, et al. (1984) Positive Selection Vectors: A Small Plasmid Vector Useful for the Direct Selection of Sau2A-generated overlapping DNA Fragments. Gene 27:323-325.
Cole, et al., "Deciphering the Biology of Mycobacterium Tuberculosis from the Complete Genome Sequence," Nature, vol. 393, Jun. 11, 1998, pp. 537-544.
Couturier, et al. (1998) Bacterial death by DNA gyrase poisoning. Trends in Microbiology 6(7):269-275.
Craine (1982) Novel Selection for Tetracycline-or Chloramphenicol-Sensitive *Escherichia coli*. J. Bacteriology 151(1):487-490.
Ebert et al. "A Moloney MLV-Rat Somatotropin Fusion Gene Produces Biologically Active Somatotropin in a transgenic pig." Molecular Endocrinology. 2:277-283, 1988.
Fleischmann et al., "Whole-Genome Random Sequencing and Assembly of Haemophilus Influenza Rd," Science, vol. 269. pp. 496-512, Jul. 28, 1995.
Gabant et al., 1997 "Bifunctional lacZ a-ccdB Genes for selective Cloning of PCR Products," Biotechniques 23:938-941.
Gabant, P., et al. (1998) Direct Selection Cloning Vectors Adapted to the Genetic Analysis of Gram-Negative Bacteria and their Plasmids. Gene 207., pp. 87-92.
Gabant, P., et al. (2000) "New Positive Selection System Based on the parD (kis/kid)System of the R1 Plasmid." BioTechniques 28:784-788.
Gabant, et al. 2001 "Use of Poison/antidote systems for selective Cloning," in Plasmid Biology 2000: International Symposium on Molecular Biology of Bacterial Plasmids, Meeting Abstracts, pp. 135-170, Plasmid 45:160-161.
Gerdes (2000) Toxin-Antitoxin modules may regulate synthesis of macromolecules during nutritional stress. Journal of Bacteriology 182:561-572.
Gossen, J.A., et al. (1992) Application of Galactose-Sensitive *E.coli* Strains as Selective Hosts for LacZ Plasmids. Nucleic Acids Res. 20,pp. 3254.
Gotfredsen, et al. (1998) The *Escherichia coli* relBE genes belong to a new toxin-antitoxin gene family. Molecular Microbiology 29(4):1065-1076.
Gronenborn (1978) Methylation of single-stranded DNA in vitro introduces new restriction endonuclease cleavage sites. Nature, 272:375-377.
Gronlund, et al., "Toxin-Antitoxin Systems Homologous with relBE of *Escherichia coli* Plasmid P307 are Ubiquitous in Prokaryotes," Journal of Molecular Biology, vol. 285, No. 4, Jan. 29, 1999, pp. 1401-1415.
Guilfoyle, R.A., and L.M. Smith (1994) "A Direct Selection Strategy for Stotgun Cloning and Sequencing in the Bacteriophage M13." Nucleic Acids Res.22, pp. 100-107.
Guzman, L.M. et al. (1995) "Tight Regulation, Modulation and High-Level Expression by Vectors Containing the Arabinose Pbad Promoter." J. Bact. 177,pp. 4121-4130.
Hammer, et al. "Genetic Engineering of Mammalian Embryos." J. Anim. Sci. 63:269-278, 1986.
Hartley, et al. 2000 "DNA Cloning Using in Vitro Site-Specific Recombination," Genome Res. 10:1788-1795.
Hebsgaard, S.M., et al. (1996) "Splice Site Prediction in Arabidopsis Thaliana Pre-mRNA by Combining Local and Global Sequence information." Nucleic Acids Research, 24(17) 3439-3452.
Henrich, et al. (1986) Use of the lysis gene of bateriophage ΦX174 for the construction of a positive selection of a positive selection vector. Gene 42:345-349.
Herrero, M., et al.(1990) "Transposon Vectors Containing Non-Antibiotic Resistance Selection markers for Cloning and Stable Chromosomal Insertion of Foreign Genes in Gram-Negative Bacteria." J. Bact. 172(11):6557-6567.
Holt, et al. (1993) A Novel Phage λ Replacement Cre-lox Vector that has Automatic Subcloning Capabilities. Gene 133:95-97.
Ioannou, et al. (1994) A new bacteriophage P1-derived vector for the propagation of large human DNA fragments. Nature Genetics 6:84-89.
Jensen, et al. 1995 "Comparison of ccd of F, parDE of RP4 , and parD of R1 using a novel conditional replication control system of plasmid R1," Mol. Microbiol. 17:211-220.
Jensen, R. B. and K. Gerdes (1995) "Programmed Cell Death in Bacteria: Proteic Plasmid Stabilization Systms." Mol. Microbiol. 17, pp. 205-210.
Kaneko, et al., "Sequence Analysis of the Genome of the Unicellular Cyanobacterium Synechocystis sp. Strain PCC6803. II.Sequence Determination of the Entire Genome and Assignment of Potential Protein-Coding Regions," DNA Research, vol. 3, pp. 109-136. 1996.
Karoui, et al. (1983) *Ham22*, a mini-F mutation which is lethal to host cell and promotes recA-dependent induction of lambdoid prophage. The EMBO Journal. 2(11): 1863-1868.
Kuhn, et al (1986) Positive-selection vectors utilizing lethality of the EcoRI endonuclease. Gene,44:253-263.
Landy (1989) Dynamic, Structural, and Regulatory Aspects of λ Site-Specific Recombination. Annu. Rev. Biochem. 58:913-949.
Lehnherr, et al. (1993) Plasmid Addiction Genes of Bacteriophage P1: *doc*, which cause cell death on curing of prophage, and *phd*, which prevents host death when prophage is retained. J. Mol. Biol. 233:414-428.
Liu (1989) DNA Topoisomerase poisons as antitumor drugs. Annu. Rev. Biochem. 58:351-375.
Maki, et al (1992) Modulation of DNA Supercoiling Activity of *Escherichia coli* DNA Gyrase by F Plasmid. The Journal of Biological Chemistry vol. 267(17):12244-12251.
Maloy, et al. (1981) Selection for Loss of Tetracycline Resistance by *Escherichia coli*. J. Bacteriology 145(2):1110-1112.
Manning, P. A., "Nucleotide Sequence encoding the Mannose-fucose-resistant Hemagglutinin of Vibrio Cholerae 01 and Construction of a Mutant," EMBL Sequence Database, Aug. 7, 1993. pp. 1-7.
Maxwell, et al. (1986) Mechanistic aspects of DNA Topoisomerases. Advan. Protein Chem. 38:69-107.
Messing, et al. (1977) Filamentous coliphage M13 as a cloning vehicle: Insertion of a *Hin*dII fragment of the *lac* regulatory region in M13 replicative form in vitro. Proc Natl. Acad. Sci. 74(9):3642-3646.
Miki, et al. (1984) Control of Cell Division by Sex Factor F in *Escherichia coli*. J. Mol. Biol. 174:605-625.
Miki, et al. (1984) Control of Cell Division by Sex Factor F in *Escherichia coli*. J. Mol. Biol. 174:627-646.

(56) References Cited

OTHER PUBLICATIONS

Moreadith, et al. "Gene Targeting in Embryonic Stem Cells: The new Physiology and metabolism." J. Mol. Med. 75:208-216, 1997.
Mullins, et al. "Perspective Series: Molecular Medicine in Genetically Engineered Animals." J. Clin. Invest. 98 (Suppl.): S37-S40, 1996.
Muyrers, et al. 2001 "Techniques: rocombinogenic engineering—new options for cloning and manipulating DNA," Trends in Biochem. Sci. 26:325-331.
Murphy, et al. (1991) pλZd39:A New Type of cDNA Expression Vector for Low Background, High Efficiency Directional Cloning. Nucleic Acids Research 19(12):3403-3408.
Nilsson, et al. (1983) An Improved Positive Selection Plasmid Vector Constructed by Oligonucleotide Mediated Mutagenesis. Nucleic Acids Research 11(22):8019-8029.
Norrander, et al. 1983 Construction of improved M13 vectors using oligodeoxynucleotide-directed mutagenesis. Gene, 26:101-106.
Ogura, et al. (1983) Mini-F plasmid genes that couple host cell division to plasmid proliferation. Proc. Natl. Acad. Sci. USA, 80:4784-4788.
pGT-N28 Vector DNA (catalog #N3728) New England Biolabs Online Catalog, Jun. 2, 1999, p. 1, www.neb.com/neb/products/nucleic/307-28.html, the whole document.
pKO Scrambler Series Gene Targeting Vectors for Knockout Mice. Stratagene Online Catalog, Jan. 1998, pp. 1-3; www.stratagene.com/cellbio/toxicology/pko.htm, the whole document.
Peakman, et al. (1992) Highly Efficient Generation of Recombinant Baculoviruses by Enzymatically Mediated Site-Specific in vitro Recombination. Nucleic Acids Research 20(3):495-500.
Pecota, et al. (1997) Combining the Hok/Sok, parDE, and pnd Postsegregational killer loci to Enhance Plasmid Stability. Applied and Environmental Microbiology 63:1917-1924.
Pierce, et al. (1992) A positive selection vector for cloning high molecular weight DNA by the bacteriophage P1 system: Improved cloning efficacy. Proc. Natl. Acad. Sci. 89(6):2056-2060.
Roberts, et al. (1992) Definition of a Minimal Plasmid Stabilization System from the Broad-Host-Range Plasmid RK2. Journal of Bacteriology Dec. 1992:8119-8132.
Roberts, et al. (1994) The parDE operon of the broad-host-range plasmid RK2 specifies growth inhibition associated with plasmid loss. J. Mol. Biol. 18; 237 (1): 35-51.
Roca, et al. (1992) A Hit-and-Run System for Targeted Genetic Manipulations in Yeast. Nucleic Acid Research 20(17):4671-4672.
Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.
Ruiz-Echevarria, et al. (1991) Structural and functional comparison between the stability systems ParD of plasmid R1 and Ccd of plasmid. F. Mol. Gen. Genet 225:355-362.
Ruiz-Echevarria, et al. 1995 "A Mutation that decreases the efficiency of Plasmid R1 Replication Leads to the Activation of parD, a Killer Stability System of the Plasmid," FEMS Microb. Letters 130:129-136.
Sadler, et al. (1980) Plasmids containing many tandem copies of a synthetic lactose operator. Gene 8:279-300.
Salmon, et al., "The Antidote and Autoregulatory Functions of the F Plasmid CcdA Protein: a Genetic and biochemical Survey" Molecular and General Genetics, vol. 244, pp. 530-538. 1994.
Sambrook, et al. (1989) Molecular Cloning: A Laboratory Manual. Cold Spring Harbor Laboratory Press, Cold Spring Harbor, NY, pp. xi-xxxviii.
Sambrook, et al. (1989) Molecular Cloning: A Laboratory Manual. Cold Spring Harbor Laboratory Press, Cold Spring Harbor, NY, pp. 4.12,A.9-A.13.
Saul, et al., "Nucleotide Sequence and Replication Characteristics of RepFIB, a Basic Replicon of IncF Plasmids," Journal of Bacteriology, vol. 171,No. 5, pp. 2697-2707, May 1989.

Schlieper, et al. 1998 "A Positive Selection Vector for Cloning of Long Polymerase Chain Reaction Fragments based on a lethal mutant of the crp Gene of *Escherichia coli*," Anal. Biochem. 257:203-209.
Seamark, R.F. "Progress and Emerging Problems in Livestock Transgenesis: a Summary perspective." Repod. Fert. Dev. 6:653-657, 1994.
Smith, et al. (1985) Modification and Selection of Human Interleukin 2 Produced in Insect Cells by Baculovirus Expression Vector. Natl Acad. Sci. 82:8404-8408.
Smith, et al. (1997) The poison-antidote stability system of the broad-host-range *Thiobacilus ferroxidans* plasmid pTF-FC2. Molecular Microbiology 26(5):961-970.
Sierra, et al. 1998 "Functional Interactions between chpB and parD, two homologous conditional killer systems found in the *Escherichia coli* chormosome and in plasmid R1," FEMS Microb. Letters 168:51-58.
Simons, R. W., et al. (1987) "Improved Single and Multicopy Lac-Based Cloning Vectors for Protein and Operon Fusions." Gene 53, pp. 85-96.
Tomb, et al., "The Complete Genome Sequence of the Gastric Pathogen Helicobacter Pylori," Nature. vol. 388, Aug. 7, 1997, pp. 539-547.
Tsuchimoto, et al. (1988) Two Genes, *pelK* and *peml*, responsible for stable maintenance of resistance plasmid R100. J. of Bateriol., 170(4):1461-1466.
Trudel, P., et al. (1996) pGATA: A Positive Selection Vector Based on the Toxicity of the Transcription Factor GATA-1 to Bacteria. BioTechniques. 20:684-693.
Tsuchimoto, et al.,"The Stable Maintenance System pem of Plasmid R100: Degradation of Peml Protein May Allow PemK Protein to Inhibit Cell Growth." Journal of Bacteriology, vol. 174, No. 13, pp. 4205-4211, Jul. 1992.
Tsuchimoto, et al. (1993) Autoregulation by cooperative binding of the Peml and PemK proteins to the promoter region of the *pem* operon. 237:81-88.
Van Reeth, T., et al. (1998) "Positive Selection Vectors to Generate Fused Genes for the Expression of His-Tagged Proteins." *Biotechniques*. 25(5):898-904.
Vernet, T., et al. (1985) "A Direct-Selection Vector Derived from pColE3-CA38 and adapted for Foreign Gene Expression." Gene 34:87-93.
Wang (1985) DNA Topoisomerases. Ann. Rev. Biochem. 54:665-697.
Yanisch-Perron, et al. (1985) Improved M13 phage closing vectors and host strains: Nucleotide sequence of the M13mp18 and pUC19 vectors. Gen, 33:103-119.
Yarmolinsky (1995) Programmed cell death in bacterial populations. Science, 267:836-837.
Yu, et al. 2000 "An Efficient recombination system for chromosome engineering in *Escherichia coli*," PNAS USA 97:5978-5983.
International Preliminary Examination Report from PCT/BE03/00045, dated Feb. 24, 2004.
International Preliminary Examination Report from PCT/BE02/00021, dated Feb. 19, 2003.
International Search Report from PCT/BE02/00021, Dated Jul. 12, 2002.
International Search Report from PCT/BE00/00151, Dated May 22, 2001.
Office Action from U.S. Appl. No. 09/634,039, Dated Dec. 16, 2004.
Office Action from U.S. Appl. No. 09/634,039, Dated Jun. 29, 2005.
Office Action from U.S. Appl. No. 09/634,039, Dated Dec. 20, 2001.
Notice of Allowability from U.S. Appl. No. 08/379,614, Dated Mar. 3, 1998.
Office Action from U.S. Appl. No. 09/225,152, dated Sep. 13, 1999.
Office Action from U.S. Appl. No. 08/379,614, Dated Aug. 27, 1996.
Office Action from U.S. Appl. No. 08/379,614, Dated Aug. 4, 1997.
Office Action from U.S. Appl. No. 09/634,039, Dated Jan. 15, 2003.
Office Action from U.S. Appl. No. 09/634,039, dated Sep. 24, 2003.
U.S. Appl. No. 09/634,039, filed Aug. 8, 2000.

REVERSIBLE, PARALLEL AND MULTITASK CLONING METHOD AND KIT

CROSS-REFERENCE TO RELATED APPLICATIONS

This application is a continuation-in-part application of U.S. patent application Ser. No. 10/526,525, entitled "REVERSIBLE, PARALLEL AND MULTITASK CLONING METHOD AND KIT," which has a 371(c) date of Aug. 26, 2005 and is a U.S. National Phase Application of International Application No. PCT/BE03/00147, entitled "REVERSIBLE, PARALLEL AND MULTITASK CLONING METHOD AND KIT," filed Sep. 3, 2003, which designated the United States of America and published in the English language, which claims the benefit of and priority to U.S. Provisional Patent Application No. 60/408,482, filed on Sep. 3, 2002. The entire content of each and every one of the applications identified above is incorporated herein by reference.

BACKGROUND

Field of the Invention

The present invention is related to a reversible, parallel and/or multitask cloning method and kit, which improves the cloning of (preferably multiple) genetic element(s) in a nucleic acid construct such as a vector or the chromosome of a cell and the rapid and efficient selection of constructs with a correct integration of said genetic element(s), either in vitro or in vivo.

More precisely, the present invention is related to integrated method and tools to construct recombinant DNA molecules (to be used as DNA vaccine or for gene therapy) without requiring the use of antibiotic(s) resistance gene(s) and without requiring the addition of one or more antibiotic(s) to the culture medium of cells submitted to this recombinant DNA method. The present invention allows to obtain the selection of recombinant host cell(s) transformed by a (exogenous) nucleic acid sequence of interest (extra-chromosomal vector containing the insert) and simultaneously stabilization (stable inheritance) of this (exogenous) nucleic acid sequence of interest into the transformed host cell(s) descendants (maintenance of the nucleic acid sequence of interest in the host cells population).

To obtain complex molecular constructs comprised of multiple genetic elements, the selection of the genetic events (insertion(s) and/or deletion(s) and/or inversions(s) of DNA fragments) that will cause the assemblage of the target construct comprised of the said genetic elements at the right position and with the right orientation is usually a time consuming procedure.

In particular, one is necessary faced with the major problem of selecting different multiple genetic events (insertion, deletion, inversion of a genetic sequence in a nucleic acid construct), possibly in the same reaction tube.

Therefore, a molecular biologist should usually obtain a genetic event (insertion, deletion, inversion of a genetic sequence in a nucleic acid construct) separately and not simultaneously in the same reaction tube and should avoid any mistake (incorrect integration of a genetic sequence in the wrong direction, etc.) during said genetic manipulation.

Generally, DNA cloning is done in two steps: firstly, a DNA fragment is inserted in vitro in a vector (i.e. an autonomously replicating genetic construct, such as a virus or a plasmid) and thereafter, a mixture containing vectors with insert and vectors alone are introduced into bacteria to increase the number of DNA molecules, these molecules are produced by these bacteria. However, these steps are rare events: 1 to 10% of the vector molecules contain an insert at the end of the experiment and 1 to 10% of bacteria receive effectively a DNA molecule (vector alone or vector+insert). Thus, it is necessary to perform an efficient selection step to isolate bacteria containing a vector and if possible, bacteria containing a vector with insert.

Antibiotic resistance is widely used and validated as selection-pressure marker for selection of bacteria containing a vector. Antibiotic resistance gene is added to the vector backbone. Only a bacterial cell having incorporated a plasmid encoding for a resistance to one specific antibiotic will divide and/or survive in a medium containing a sufficient amount of this antibiotic, allowing to easily select transformed host bacterial cells, and to maintain them in culture.

However, the use of antibiotics and antibiotics resistance sequences present several drawbacks.

Firstly, the transfer of this antibiotic(s) resistance to other bacteria is possible. Indeed, bacteria are exchanging DNA even between different species (conjugation, transduction, passive or active DNA uptake). During these DNA exchanges, plasmids play a major role especially in the case of DNA conjugation. When antibiotic(s) resistance genes are used in recombinant DNA techniques, plasmids contain these genes and when used in applications related to humans or to animals (food industry, DNA vaccine, etc.), it exists a risk to obtain a transfer of these resistance genes to other bacteria including pathogen bacteria.

Secondly, the use of antibiotics in recombinant DNA techniques is not always very efficient (due to spontaneous resistant mutants for example) and could be costly. Moreover, some antibiotic resistance have been suggested to burden a lot of the host cell energy limiting the efficacy of the host cell to produce biopharmaceutical compounds.

More recently, the tendency is to avoid the use antibiotics in applications related to human or animals (from the food industry to the production of vectors, or vectors for DNA vaccination). Consequently, the FDA (Food and Drug Administration in USA) and EMA (European Medicine Agency) recommend avoiding the use of antibiotics in this kind of applications.

Besides antibiotics, several operons are known to encode both a protein that is toxic to a cell and its specific antitoxin. These systems, sometimes called "poison-antipoison," "Toxin-Antitoxin," or "plasmid addiction," are now used for plasmid stabilization.

The U.S. Pat. No. 5,888,732, which is incorporated by reference in its entirety, discloses the "Gateway technology," wherein a donor vector comprises a donor insert (e.g. a DNA fragment of interest), placed between two recombination arms that do not recombine with each other. This gene of interest can be inserted at a defined position into a receiving (acceptor) vector having the corresponding recombination arms. In this technology, the donor and acceptor vectors comprise each a different gene encoding a resistance to an antibiotic. When these vectors are transformed in a sensitive host cell, the cells containing one of these vectors are selected by plating it on a medium containing the corresponding antibiotic.

According to one embodiment of the Gateway technology, besides the presence of a selectable marker, the acceptor vector comprises a gene encoding a toxin placed between the recombination arms. After in vitro recombination between the donor and the acceptor vectors, the DNA mixture is transformed into bacterial cells. This DNA mixture contains different kinds of DNA molecules: donor vector, acceptor vector, co-integrate vector (donor vector associated to acceptor vector), acceptor vector with the DNA fragment of interest and by-product (donor vector without the DNA fragment of interest). Thus, it is necessary to select bacteria containing acceptor vector having integrated the DNA fragment of interest during recombination (replacement of the gene encoding the toxin by the DNA fragment of interest). On one hand, plating the transformed bacteria on a medium containing the antibiotic corresponding to the antibiotic resistance gene of the acceptor vector allows to get rid of bacteria having received a donor vector or a by-product. On the other hand, the presence of the gene encoding the toxin in the original acceptor vector eliminates bacteria containing this acceptor vector (without DNA fragment of interest) or co-integrates. Therefore, thanks to the combined use of antibiotics and gene encoding the toxin, only bacteria containing the acceptor vector having integrated the DNA fragment of interest will grow on the plates.

However, none of the prior art discloses efficient and rapid "antibiotic-free" method and tools allowing easy transfer of a DNA fragment of interest from one vector to another by recombination and subsequent selection of the cells having incorporated the desired plasmid (which has incorporated a gene of interest at a correct position and in a correct reading orientation).

Aims of the Invention

The present invention aims to provide new and improved method and tools that do not present the drawbacks of the state of the art and which improve positive selection and consecutive stabilization of recombinant clones, especially a method and tools that are more simple, more efficient, less labor intensive and that present an improved speed and yield and that facilitate nucleic acids cloning and subsequent expression by cells.

More particularly, the aim of the invention is to propose a method and tools that are based upon an "antibiotic-free" efficient selection of recombinant cells having incorporated correctly an (exogenous) insert (possibly encoding a desired molecule of interest) in a vector after recombination, this kind of insert molecule being possibly used as a DNA vaccine or for gene therapy.

SUMMARY OF THE INVENTION

In the method and kit described hereafter, the person skilled in the art uses specific genetic constructs, which are the tools for performing the cloning and selection method according to the invention. Said tools are genetic constructs that could be integrated in vector(s) (plasmid(s) or virus(es), including bacteriophage(s)) or in the chromosomal genome of a cell suitable for obtaining the cloning and selection of the correct assemblage of various genetic elements. All these methods and systems allow the assemblage of one or more foreign genetic element(s) (target sequences of interest) in said nucleic acid construct vector or chromosome of a cell at specific sites. The integration of a foreign (preferably autologous) genetic element the nucleic acid construct of the invention could be done by techniques known to the person skilled in the art such as, but not limited to classical restriction/ligation, site specific recombination, TOPO cloning and homologous recombination. The assemblage of genetic elements can involve insertion(s), deletion(s) and/or inversion(s) of nucleotide sequences. In the method according to the invention, the selection of correctly inserted sequences is obtained by using specific markers, which are nucleotide sequences encoding molecules that are toxic for a cell or molecules which are inhibitors of such toxic molecules and/or block to toxic activity of such molecules expressed in the cell. Preferably, said molecules are either poison(s), and/or inhibitor(s) to poison(s), preferably selected from (but not restricted to) the group consisting of the following poison/antidote systems: Ccdb/Ccda, Kid/Kis, Hok/Sok, Doc/Phd, RelE/RelB, PasA/PasB/PasC, MazE/MazF, ParE/ParD.

In the method according to the invention, said foreign nucleotide elements are advantageously linked (at its 3' or 5' or both ends) to one or more promoter/operator nucleotide sequences, such as, but not limited to, constitutive promoters allowing the expression of a target nucleotide sequence incorporated in the nucleic acid construct according to the invention, when they are disposed according to the suitable and requested reading orientation.

In the method according to the invention, the person skilled in the art uses suitable cell strain(s) (prokaryotic and/or eukaryotic) which are either resistant or sensitive to one or more of said toxic molecules in order to obtain and select recombinant(s). The properties of cell strains can for example be due to the existence of gene(s) coding for poison and/or antidotes and integrated in the chromosome(s) of a cell or presented in episomal sequences such as plasmids.

A first aspect of the present invention is related to a reversible cloning method and kit for which several specific preferred examples are described in details hereafter, in reference to the FIGS. 2 to 5.

The elements used in the method of the invention are specific cells and a genetic preferably integrated in a vector or a chromosome of a cell comprised of either a promoter/activator sequence 11 disposed upstream of a first and a second nucleotide sequence (1, 2) encoding two different toxic molecules (such as a poison 1 and a poison 2) (FIG. 2, left), or a first promoter/activator sequence 11 disposed upstream of a first nucleotide sequence 1 encoding a toxic molecule (such as a poison 1) and, disposed in the opposite reading direction of the first promoter/activator sequence 11, a second promoter/activator sequence 12 disposed upstream of a second nucleotide sequence encoding an antidote 2' to a second toxic molecule (such as poison 2) (FIG. 3, left), or a promoter/activator sequence 11 disposed upstream of a first and a second nucleotide sequence (1, 2') encoding, respectively, a first toxic molecule (such as poison 1) and an antidote to a second toxic molecule (such as poison 2) different from said first toxic molecule (FIG. 4, left).

The terms "a nucleotide sequence encoding a toxic molecule or an antidote to a toxic molecule" also include sequences comprising multiple coding portions encoding several identical toxic molecules.

The insertion of a foreign target nucleotide sequence (A) "in" or as "a replacement" of the nucleotide sequence encoding a toxic molecule element will allow either:

the inactivation of the nucleotide sequence 1 encoding the first toxic molecule, plus the activation or maintenance of the activation of the sequence 2 encoding the second toxic molecule (FIG. 2); or the inactivation of the first nucleotide sequence 1 encoding the first toxic molecule, plus the inactivation of the nucleotide sequence 2 encoding the antidote to the second toxic molecule (FIG. 3); or the inactivation of the first nucleotide sequence 1 encoding the first toxic molecule (FIG. 4).

The inserted foreign genetic element(s) (target sequence) may be a regulatory sequence or gene(s) of interest (possibly linked to one or more promoter/operator sequences).

The selection of the genetic event (insertion) can be obtained in a cell strain sensitive to the first toxic molecule 1 (FIGS. 2, 3, 4) and possibly resistant to the second toxic molecule 2 (FIG. 2).

However, the said genetic event (insertion or replacement) is reversible through the replacement of the inserted element (target sequence) by the element that had been deleted following the recombination and insertion made in the first step. This reverse reaction deletion of a target sequence is selected in a strain both resistant to the toxic molecule 1 and sensitive to the toxic molecule 2 (FIGS. 2, 3, 4) plus, possibly, producing the toxic molecule 2 (FIGS. 3, 4).

This reversible cloning and selection method is also suitable for obtaining an inversion of an integrated genetic element. A specific example is described in details hereafter, in reference to the FIG. 5. Indeed, the orientation of a sequence of interest can be reversed through the method of the invention (preferably following the insertion step of FIG. 4) or through a direct insertion of the target sequence between two different antidote sequences (1', 2'). Said genetic element (target sequence) associated to a promoter/operator (either at its 3' or 5' end), is initially integrated between two nucleotide sequences (1', 2') encoding respectively two different antidotes to two different toxic molecules 1 and 2. Said two nucleotide sequences (1', 2') encoding the two different antidotes are disposed in opposite reading orientations (disposed upstream and downstream the target nucleotide sequence in opposite divergent reading orientation). This construct allows to select for the recombination event(s) which will cause the target nucleotide sequence of interest and its associated promoter to have either the same orientation as the nucleotide sequence 1' encoding the first antidote to the first toxic molecule (selection done in a strain both sensitive to and producing poison 1) or the same orientation as the nucleotide sequence 2' encoding the second antidote to the second toxic molecule (selection done in a strain both sensitive to and producing poison 2). (see WO 02/066657 incorporated herein by reference in its entirety).

The above-mentioned reversible cloning and selection method and elements (nucleic acid construct or vector and specific cells strains) can also be used in a parallel and/or multitask cloning and selection method described hereafter (in details in the following example in reference to the FIG. 1).

The assemblage of multiple foreign genetic elements (different target sequences) in the vector or in the chromosome of a cell (either in vitro or in vivo) and the selection of the correct assemblage is obtained by the use of multiple nucleic acid construct comprising sequences encoding one or more (different or identical) toxic molecules and/or their antidotes. According to the type of the nucleic acid construct and the type of selective markers (encoding toxic molecules(s) and/or antidote(s) to toxic molecule(s)), the person skilled in the art can select the suitable events of insertion(s), deletion(s) and/or inversion(s) applied with said multiple genetic element(s).

Said cloning and selection method may require multiple steps possibly performed (sequentially) in the same reaction tube or inside a single cell.

Said method can be combined with the steps and means for performing in vitro protein synthesis (using in vitro transcription and translation kits).

Another aspect of the present invention is related to the algorithms, computer programs, and data bases (comprised of codes and means possibly stored in a computer readable medium) that can assist performing one or more step(s) of the method according to the invention. Said algorithms, data bases, and program codes means are used to define the correct combination of (but not limited to):

suitable markers (encoding the toxic molecule and/or the antidotes to said toxic molecule);

suitable cell strain(s) for selecting the suitable genetic events;

suitable pre-starting nucleic acid construct(s);

suitable genetic element(s) (target nucleotide sequences and/or their operator/promoter sequences) to be inserted, deleted and/or reversed;

reaction mixture (including but not restricted to recombines mixtures, buffer, media, enzymes, . . . ) that are necessary for the assemblage/production of the molecular construct.

The algorithms, computer programs, and data bases are also able to control one or more step(s) of the method according to the invention, possibly performed by automate(s).

Another aspect of the present invention is related to kits of parts (cloning and/or selection kits) comprising the suitable elements for performing the method according to the invention, in particular computer programs mentioned above, nucleic acid construct(s), cell strain(s) and/or usual products and media used in the cloning and selection techniques.

Another aspect of the present invention is related to automates allowing to perform the method according to the invention and using the above-mentioned kit(s) of parts. Said kit(s) of parts (cloning and selection kits, combined with adequate media, cells and media present in vitro transcription and translation kits) and automates could also comprise other elements, such as a buffer solutions, pipetting element(s), primers for genetic amplification, cell culture media and means for recording results and for the storage of data.

A further aspect of the present invention is a genetic construct or (autonomously replicating) vector (such as viruses (including phages) or plasmids) comprising A first nucleotide sequence encoding (coding for) a first poison protein, possibly this sequence being duplicated and placed in tandem;

Means to conditionally inactivate the synthesis of this first poison protein, preferably a pair of two different (specific) recombination (or restriction) sites or recombination arms, disposed upstream and downstream this first nucleotide sequence encoding (coding for) this first poison protein;

A second nucleotide sequence encoding (coding for) an antidote protein to a second poison protein (different from the first poison protein: i.e. a second poison protein having a different cell target that the first poison protein).

Preferably, this genetic construct is in the form of (or is present in) a plasmid and the mentioned nucleotide sequences correspond to DNA molecules present in this construct and this genetic construct comprises also suitable genetic elements (like promoter/activator sequences) for the expression of the nucleotide sequence including the gene product of interest.

A complementary aspect of the present invention is related to a method for (sub-) cloning and stabilizing a (exogenous) nucleic acid sequence of interest (insert, preferably a coding sequence encoding a polypeptide that can be present an industrial (enzyme), prophylactic or therapeutic application, especially as a vaccine for a human or for animal) into a cell, this method comprising the steps of:

a) preparing (and amplifying) a DNA sequence of a receiving (acceptor) vector (preferably the genetic construct (plasmid) of the invention) comprising:

a (at least one) first nucleotide sequence encoding (coding for) a first poison protein;

a first pair of two different recombination or restriction sites or arms (allowing conditional inactivation of the synthesis of this poison protein), possibly several (and different) poison proteins(s) encoded by different sequences, possibly present simultaneously in this receiving vector, these sites being preferably a first pair of two (specific) different recombination sites, more preferably a first pair of two recombination sites or arms that do not react with each other, or a pair of two unique and different restriction sites or arms, the first site or arm being disposed upstream the said nucleotide sequence encoding (coding for) the first poison protein and the second site or arm being disposed downstream the said nucleotide sequence encoding (coding for) the first poison protein;

a second nucleotide sequence encoding (coding for) an antidote protein to a second poison protein;

b) performing a recombination event with methods well known by the person skilled in the art (including In-fusion technique (Clontech), in vivo recombination, etc.) between this receiving (acceptor) vector and a donor vector, this donor vector comprising the nucleic acid sequence of interest (insert) located between a second pair of two (specific) different recombination or restriction sites or (recombination) arms (wherein the second pair of recombination (or restriction) sites or arms being compatible with (specific to) the first pair of recombination or (restriction) sites or arms);

c) obtaining a chimeric nucleic acid molecule comprising the nucleic acid sequence of interest (insert);

d) introducing (transforming) the obtained recombination mixture (including the chimeric molecule) in cell(s) carrying (preferably in their chromosome) a nucleotide sequence encoding (coding for) this second poison protein (these host cell(s) correspond to cells comprising the chimeric nucleic acid molecule, correspond to cells comprising the receiving vector or correspond to cells comprising the donor vector or co-integrate of donor and receiving vectors);

e) obtaining, an expression (synthesis) of the toxic activity of this first (if present) poison/protein and this second poison protein and of the antitoxin protein to said second poison protein in the (transformed) cells;

f) obtaining (recovering) cells surviving to the toxic activity of these first and second poison proteins and;

g) growing (and collecting or harvetizing) the recovered surviving cells comprising the nucleic acid sequence of interest (insert) under selective pressure (surviving to the expression) of this second poison protein.

Advantageously, (at least) steps a) to g) of the method of the invention are carried-out without the use of antibiotics (addition of one or more (above mentioned) antibiotic(s) to the cells medium).

Advantageously, the present method is performed with (all) the preferred plasmids of the present invention.

Preferably, in the method of the invention, the insertion step of a nucleic acid sequence of interest (insert) is performed by the excision of the first nucleotide sequence encoding (coding for) the first poison protein and by its replacement by this nucleic acid sequence of interest (insert), through the use of the (recombination or restriction) sites or (recombination) arms present in the vectors according to the present invention.

Preferably, in the genetic construct and method of the invention, the first poison protein is selected from the group consisting of CcdB, Kid (PemK), Doc, RelE, MazF, PasA and ParE proteins, preferably Kid (PemK) protein and the corresponding antidote protein to the second poison protein is selected from the group consisting of CcdA, Kis (PemI), Phd, RelB, MazE, PasB/PasC and ParD proteins, preferably Kis (PemI) protein with the provisio that this first poison protein and this second poison protein are different (that do not bind by the same mechanism to the same target and that are not inactivated by the same antidote protein).

In the method and construct of the invention, the first poison protein and first antidote protein correspond to the following preferred couple of poison/antidote proteins: CcdB/CcdA, Kid (PemK)/Kis (PemI), Doc/Phd, RelE/RelB, MazF/MazE, PasA/PasB/PasC and ParE/ParD proteins, preferably Kid (PemK)/Kis (PemI) proteins.

More preferably, in the genetic construct and method according of the invention, the first poison protein is Kid (PemK) protein and/or the antidote protein to the second poison protein is CcdA protein, but the preferred alternative is also possible with a selection of CcdB protein, as the first poison protein and the selection of Kis (PemI) protein as the antidote protein to the second poison protein (being Kid (PemK) protein).

However, the first preferred alternative is preferred, because it is known that the CcdB poison/protein is not affecting eukaryote cell. This means that the construct according to the invention will lead to a deletion of poison/protein sequence susceptible to kill eukaryote cells.

In the method and construct according to the invention, the second poison/protein and second antidote/protein correspond also to the above-described preferred couple of poison/antidote proteins: CcdB/CcdA, Kid (PemK)/Kis (PemI), Doc/Phd, RelE/RelB, PasA/PasB/PasC MazF/MazE and ParE/ParD, preferably CcdB/CcdA.

Preferred means to conditionally inactivate the first nucleotide sequence encoding (coding for) the first poison protein of the genetic construct of the invention are selected from the group consisting of recombinases, integrases, nucleases and restriction endonucleases and ligases, being preferably recombinase (i.e. an enzyme which catalyzes the exchange of DNA fragments at specific recombination sites by homologous recombination or by site-specific recombination and specific recombination sites (preferably att sites for recombination) in the genetic construct, compatibles with the use of these recombinases, integrases, nucleases, restriction endonucleases and ligases.

A preferred example of recombinase to be used in the method of the invention is the recombinase "Cre" available commercially, a protein from the bacteriophage P1 that catalyzes the exchange (recombination) between 34 bp DNA sequences called loxP (locus of crossover) sites. A preferred example of integrase to be used in the method of the invention is the protein Lamda Int obtained from a bacteriophage that mediates the integration of Lamda genome into the *E. Coli* chromosome.

Advantageously, targets of these means that conditionally inactivate the first poison protein of the genetic construct of the invention correspond to two specific sites, preferably two att sites (or recombination arms), that are different, preferably being two recombination sites (or arms) that do not react with each other, or two unique restriction sites.

Preferably, the first specific site (or arm) is disposed upstream the nucleotide sequence encoding (coding for) the poison protein, and the second specific site (or arm) is disposed downstream the nucleotide sequence encoding (coding for) the poison protein (i.e. the nucleotide sequence encoding (coding for) the poison protein is disposed between these two different recombination sites (or arms)).

Alternatively, in the genetic construct and method of the invention one or the two specific sites (or arms) is disposed within the said nucleotide sequence encoding (coding for) the first poison protein and the integration (insertion) of a nucleic acid of interest (insert) at this specific site will render impossible the synthesis of the corresponding poison protein.

Advantageously, the antidote sequence carried by the genetic construct according to the invention is not toxic for an eukaryote cell.

Advantageously, the genetic construct according to the invention does not carry (and the method steps (at least the cloning and selection steps of this method) are not based upon (do not require the use of) genes encoding (coding for) for antibiotics (also called hereafter antibiotics resistance sequences), especially based upon the following antibiotics: aminoglycosides (such as kanamycin), ansamycins, carbacephem, carbapenems, cephalosporins, glycopeptides antibiotics (such as vancomycin), macrolides, monobactams (such as aztreonam), penicillins (such as ampicillin), polypeptides antibiotics (such as bacitracin, colistin and polymixin B), quinolones, sulfonamides, tetracyclines and other non-classified antibiotics (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin/rifampin, thiamphenicol, tinidazole, dapsone, and clofazimine).

Preferably, in the genetic construct and the method according to the invention, the second nucleotide sequence encoding (coding for) an antidote protein to the second poison protein is disposed upstream this nucleotide sequence encoding (coding for) a first poison protein.

Preferably, in the genetic construct and the method according to the invention, the nucleotide sequence encoding (coding for) the first poison protein and the nucleotide sequence encoding (coding for) the antidote protein to the second poison protein are co-expressed: under the control of the same promoter and are in the same (reading) orientation.

Alternatively, in the genetic construct and the method according to the invention, the nucleotide sequence encoding (coding for) the first poison protein and the nucleotide sequence encoding (coding for) the antidote protein to the second poison protein are expressed under the control of two identical promoters, and preferably are in the same (reading) orientation.

Alternatively, in the genetic construct and the method according to the invention, the nucleotide sequence encoding (coding for) the first poison protein and the nucleotide sequence encoding (coding for) the antidote protein to the second poison protein are independently expressed and/or are under the control of different promoters and in different (reading) orientations.

Another aspect is related to a cell, preferably *E. coli* cell transformed by this (exogenous: i.e. exogenous to the genome of the cell) nucleic acid of interest (insert) and obtainable by the method of the invention.

A further aspect of the present invention is related to the host cell of the genetic construct or (autonomously replicating) vector according to the invention, this host cell comprising integrated in its genome a third nucleotide sequence encoding (coding for) an antidote protein to the first poison protein and preferably integrated also in its genome a fourth nucleotide sequence encoding (coding for) a second poison protein.

Preferably, this host cell is the host of the preferred genetic construct or autonomously replicating vector according to the invention comprising a first nucleotide sequence encoding (coding for) a first poison/protein being Kid (PemK protein), wherein the second nucleotide sequence encoding (coding for) CcdA antidote protein to the second poison/protein CcdB, which means that this host cell further comprises integrated in its genome third nucleotide sequence encoding (coding for) the Kis (PemI) antidote protein and a fourth nucleotide sequence encoding (coding for) a poison/protein being the CcdB poison/protein.

The term "cell" corresponds to any prokaryotic or eukaryotic cell or organism that can be a recipient of a recombinant cloning product (exogenous nucleic acid sequence of interest or insert).

A further aspect is related to a nucleic acid construct or autonomously self-replicating vector that does not comprise any antibiotic(s) resistance gene, especially a construct or vector being a DNA vaccine for humans or animals, preferably in the form of a plasmid obtainable from this host cell of the invention, preferably a construct or vector comprising the nucleotide sequence encoding (coding for) an antidote protein, preferably CcdA antidote (which is not toxic for an eukaryote cell), to a poison protein (preferably CcdB protein) and the nucleic acid sequence of interest (insert) comprising a nucleotide sequence encoding a protein of interest, this nucleotide sequence being under the control of a eukaryote promoter (i.e. a promoter active in an eukaryote cell and allowing the synthesis of the protein of interest in an eukaryote cell).

The genetic construct and cells according to the invention is preferably present in a kit or device (automate able to carry out one or more (or all) of the steps of the method of the invention), with one or more media (or reactants) and software used to carry out the steps of the method according to the invention, such as means to inactivate the synthesis of the poison protein (one or more recombinase(s), endonuclease(s), integrase(s), ligase(s), . . . ), solid support(s) (such as multiwell plates) for the cells, pipetting means, software for controlling the apparatus of the invention and/or for assisting the consumer to complete the method steps, etc.).

The present invention will be described in detail in the following examples, in reference to the enclosed figures presented as non-limiting illustration of the various aspects of the present invention.

DETAILED DESCRIPTION OF THE INVENTION

Figure 1:
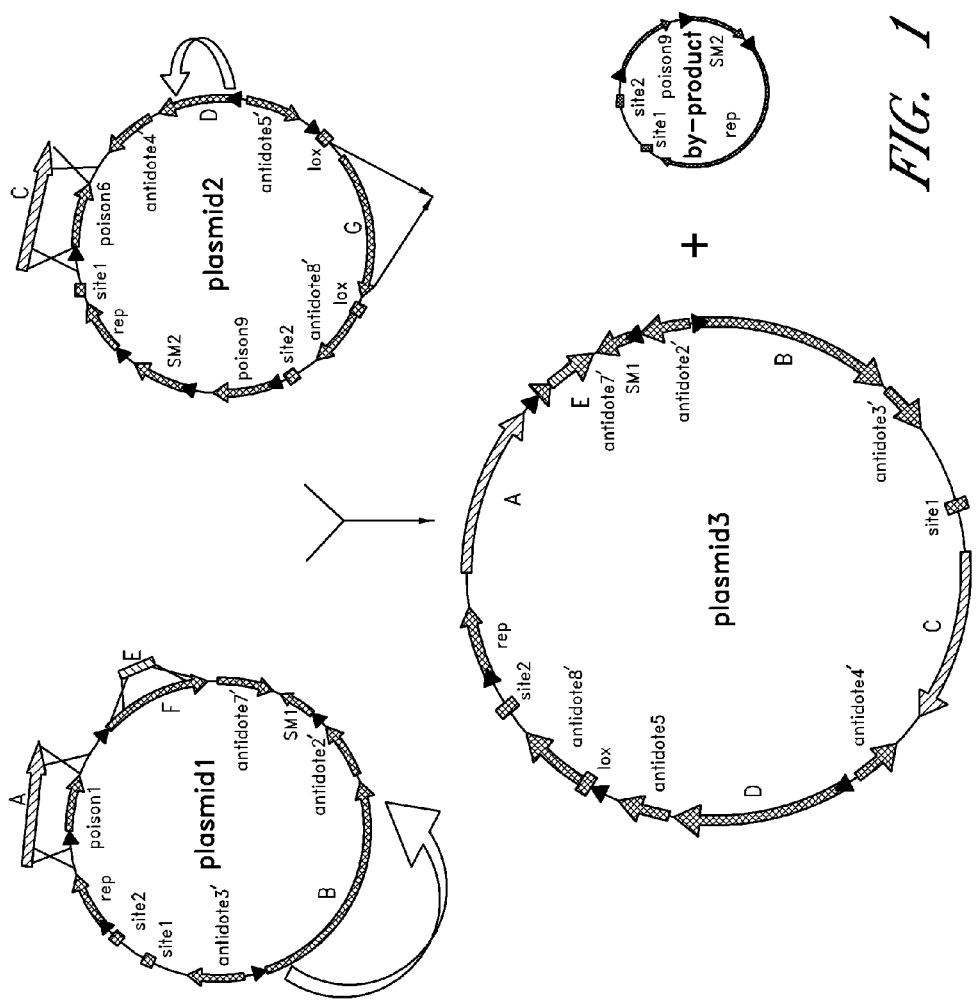
FIG. 1 is an example of complex genetic construct obtained by parallel and multiple genetic events performed by the method of the present invention.

The present invention allows the making of complex genetic constructions through the use of (i) simultaneous and (ii) parallel events (the various recombinations and selection events present almost the same frequency). The "multitask" nature of the invention is defined as follows: for example, the invention allows to perform the insertion of genetic elements A and C, the deletion of genetic elements E and F, and the inversion of genetic elements B and D, some or all events (FIG. 1) being performed simultaneously in vitro (i.e., in the same tube) or in vivo (i.e., in the same organism). The final product of the above-mentioned events is a complex construct comprised of the genetic elements A, B, C, and D, all with the same orientation. The simultaneous selection of several genetic events (e.g., here, insertions, deletions, inversions, recombinations) is achieved through the use of a different selective marker (here poisons and antidotes genes for example) for each of the events. Filled black arrows represent promoters.

Plasmid 1 is amplified in a strain resistant to poison 1. Plasmid 2 is amplified in a strain resistant to poisons 6 and 9. Plasmid 3 is selected in a strain:
  sensitive to poisons 1 and 6 (for the selection of the insertion of genetic elements A and C),
  sensitive to poisons 3 and 5 (for the selection of the inversions of genetic elements B and D),
  sensitive to poisons 7 and 8 (for the selection of the deletions of genetic elements E and F),
  sensitive to poison 9 (for the selection of the recombination event between the construct made from plasmid 1 and the construct made from plasmid 2),
  and producing poison 3, poison 5, poison 7 and poison 8.

Realization of each "recombination" event can be done through techniques such as, but not limited to, classical restriction/ligation, site-specific recombination, or homologous recombination. Specificity of each genetic event (insertion, deletion, inversion, etc.) is insured by the specificity of the recombination event. For example, specificity of an insertion (both the location of the insertion and the orientation of the insert (target nucleotide sequence)) can be achieved by the use of different DNA sequences bordering both the insertion site and the fragment to be inserted (these DNA sequences can be selected by the man skilled in the art for performing said recombination event). These flanking sequences form either different site-specific recombination elements (in the case of site-specific recombination) or different elements of homology (in the case of homologous recombination). The simultaneous selection of several genetic events (e.g., an insertion, a deletion, and an inversion) is achieved through the use of a different selective marker for each of the events. As each of the genetic events is rare by nature, the selection for the simultaneous presence of all events requires the use of very efficient selective markers (e.g., but not limited to, antidote/poison genes).

The parallel cloning nature of the invention is defined as follows: N different genetic constructs that are produced in the same reaction mix (i.e., in the same tube) through the multitask process described above can be pre-designed such that their assemblage (here, the assemblage of the construct made from plasmid 1 with the construct made from plasmid 2) can be generated through recombination events as well. In other words, N−1 genetic constructs can be viewed as donors and 1 construct as a receptor. For example, N constructs can be combined through the use of n−1 selective markers for the selection of n−1 recombination events (FIG. 1).

Furthermore, the invention allows to use the products of the multitask/parallel cloning process as building blocks of new reactions. Indeed, a construct produced through the invention is a unique combination of building blocks that can be re-used for new (and different) constructs; i.e., the process is reversible and extendable, as shown in the FIGS. 2 to 4.

Figure 2:
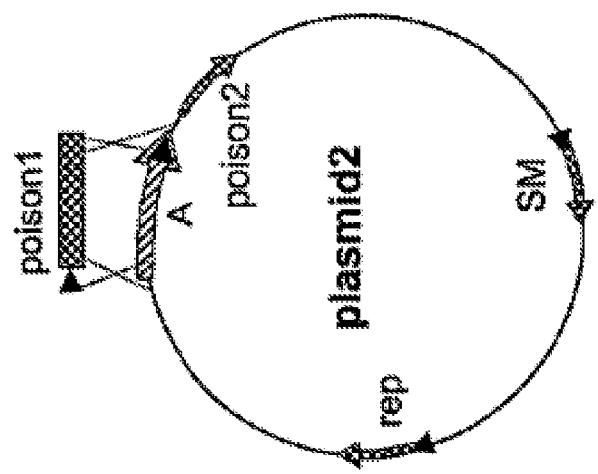
FIGS. 2 to 5 are examples of reversible cloning and selecting method and kit according to the invention.
Figure 2:
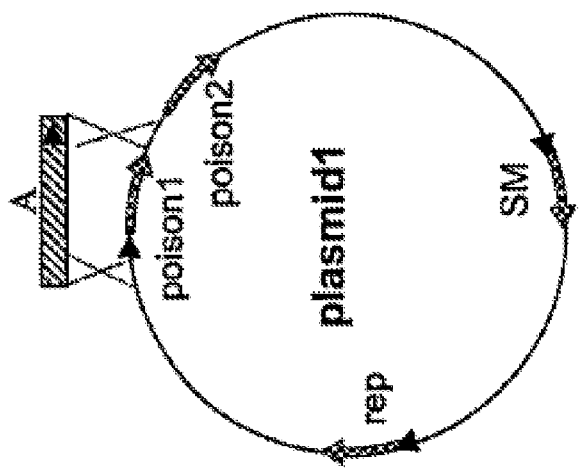

In FIG. 2, the DNA fragment to be inserted encodes for a target sequence of interest plus a promoter sequence located at its 3' end. The nucleic acid construct comprising the adequate insertion is selected by the deletion of the nucleotide sequence 1 encoding poison 1 in a strain sensitive to it but resistant to poison 2. The deletion of the target sequence (DNA fragment A) for re-use of the building block is achieved through the insertion of the DNA fragment initially removed (i.e., nucleotide sequence 1 encoding poison 1 with a promoter at its 5' end). This reverse event is selected in a strain sensitive to poison 2 and resistant to poison 1. Plasmid 1 is amplified in a strain resistant to poison 1. Plasmid 2 is amplified in a strain resistant to poison 2.

Figure 3:
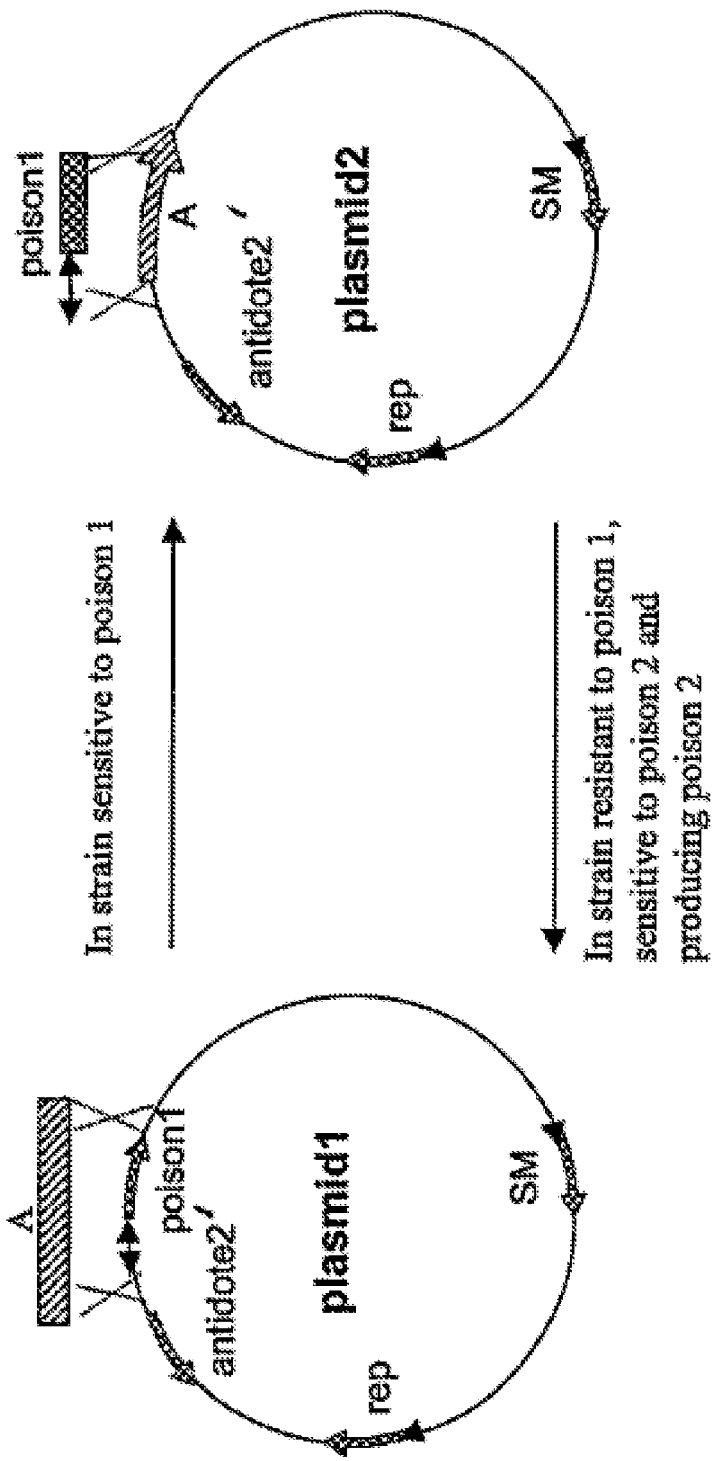

In FIG. 3, the insertion of the target sequence (DNA fragment A) is selected by the deletion of the nucleotide sequence 1 encoding poison 1 in a strain sensitive to it. The deletion of the DNA fragment A for re-use of the building block is achieved through the insertion of the DNA fragment initially removed (i.e., poison 1 with, at its 5' end, two promoters in opposite directions). This reverse event is selected in a strain allowing the conditional expression of poison 2, sensitive to poison 2, and resistant to poison 1. Plasmid 1 is amplified in a strain resistant to poison 1. Plasmid 2 is amplified in any strain whose viability is independent from the presence or absence of plasmid 2.

Figure 4:
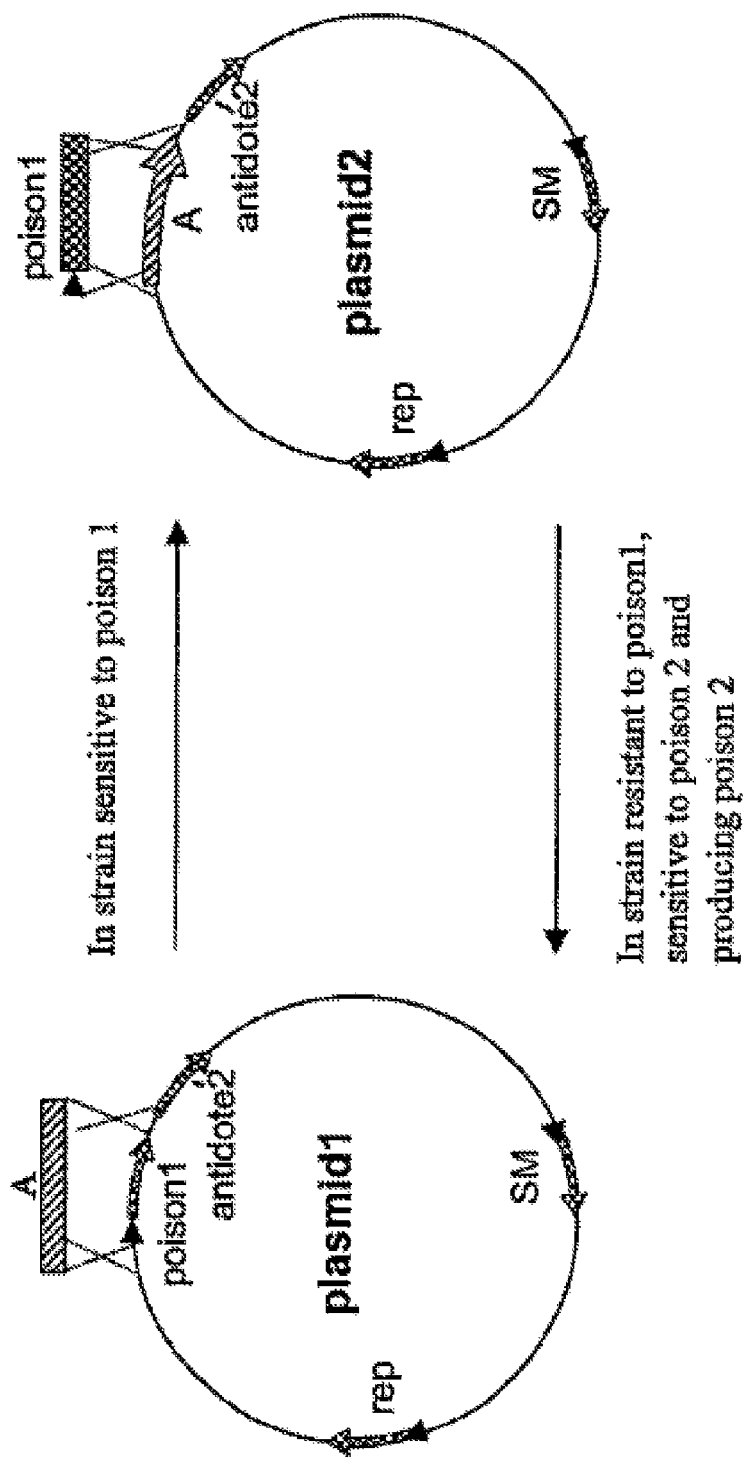

In FIG. 4, Plasmid 1 encodes both poison 1 and antidote 2 that are organized as an operon. The insertion of the target sequence (DNA fragment A) is selected by the deletion of the nucleotide sequence encoding poison 1 in a strain sensitive to it. The deletion of the target sequence (DNA fragment A) for re-use of the building block is achieved through the insertion of the DNA fragment initially removed (i.e., nucleotide sequence encoding poison 1 with a promoter at its 5' end). This reverse event is selected through the activation of the nucleotide sequence encoding antidote 2 in a strain allowing the conditional expression of poison 2, sensitive to poison 2, and resistant to poison 1. Plasmid 1 is amplified in a strain resistant to poison 1. Plasmid 2 is amplified in any strain whose viability is independent from the presence or absence of plasmid 2.

Figure 5:
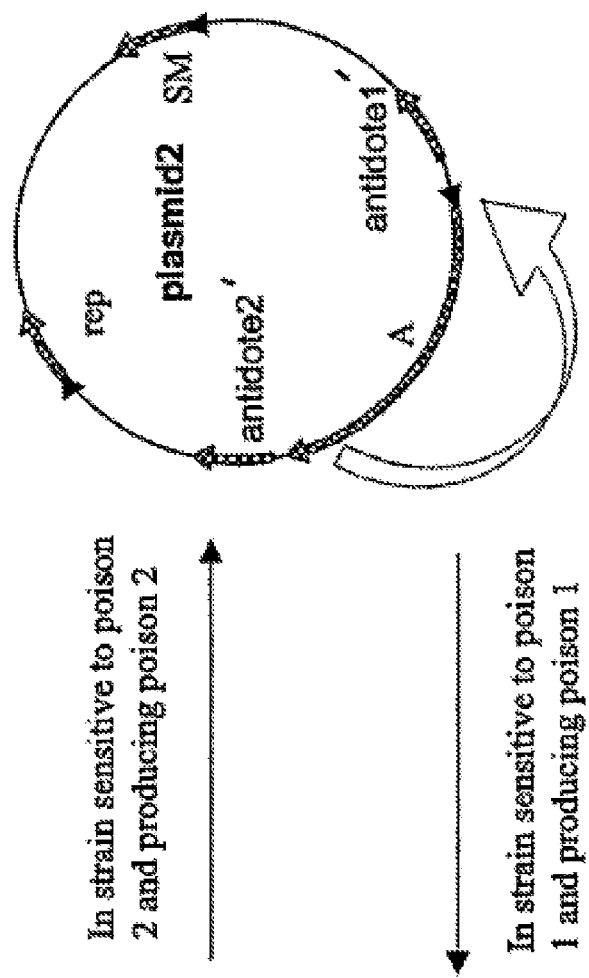
Figure 5:
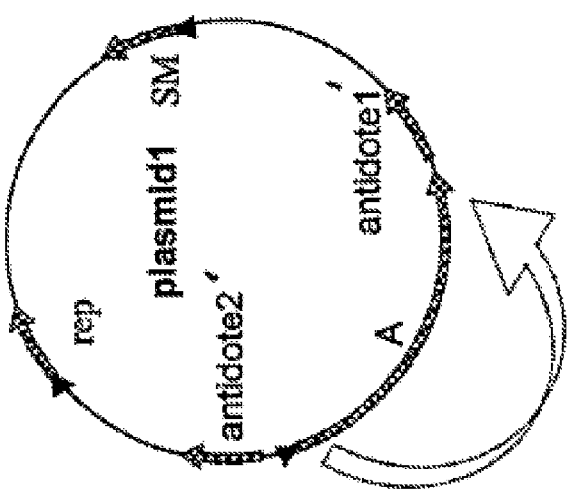

In FIG. 5, the target sequence (DNA fragment A) contains a promoter allowing the production of an antidote. The inversion of the DNA fragment A is selected using a strain allowing the conditional expression of poison 2 and sensitive to it. The reverse event is selected in a strain allowing the conditional expression of poison 1 and sensitive to it.

In other words, constructs produced through the invention are not dead-end products (i.e., useful for the only use they have been produced for); they can be recycled. This emphasizes the importance of the software component of the invention because it allows to create not only a data base of building blocks, but also of products that are followed up and stored (virtually in computers, and physically in freezers or other devices) for potential future uses. Because the software tracks the features of each building block and product, it also identifies those elements that are (i) necessary and (ii) inter-compatible for future and new multitask/parallel/reversible processes.

The inventors developed a method allowing to easily transfer a (exogenous) DNA fragment (or insert) into another genetic construct without the use of antibiotic resistance genes. The term "insert" corresponds to a desired DNA segment which one wishes to manipulate by the method of the present invention. This insert may comprises one or more genes, one or more promoter sequences (5'-regions of genes located proximal to the start codon of these genes), preferably a eukaryote promoter, an origin of replication or others (exogenous) nucleotide elements.

This is especially advantageous in the field of recombinant DNA technology, as it allows to modify a promoter sequence, to tag a protein sequence (to aid in protein purification, for example by addition of His residues, or to allow a tracking of proteins in a cell), to fuse a protein sequence, to obtain synthesis of probes, to obtain templates for DNA sequencing, to obtain an identification of protein coding regions, to provide high amount of a (exogenous) nucleic acid sequence of interest and to allow high-throughput (even automatic) transfer of one or more nucleic acid sequence(s) (of interest) into a cell and to obtain corresponding expression of one or more peptide(s) of interest encoded by one or more exogenous sequence(s).

Preferably, this insert is a coding sequence that can be used as a vaccine or that codes for a molecule involved in the production of a vaccine or that could be used as a vaccine for human or animals.

The inventors have discovered that this method of DNA transfer can be advantageously simplified and be combined to (be compatible with) a method allowing an efficient plasmid stabilization without additional background.

The inventors have observed unexpectedly that the simultaneous use of two poison proteins (in the same selection sequence and not step by step) is working without any important background.

The inventors have advantageously avoid the use of antibiotics in the method of the invention, at least for selecting the genetic construct or vector designed to receive (exogenous) the nucleic acid sequence of interest (insert), and in steps for the selection of cells comprising this insert (exogenous nucleic acid sequence of interest) following transformation and plasmid stabilization by a prolonged culture of this transformed cell.

More precisely, the inventors have found that an antibiotic-free method based on a single use of poison-antidote couples, such as CcdB/CcdA, Kid/Kis, Doc/Phd, MazE/MazF and ParD/ParE, allows this simplification and can be used for an efficient transformation and maintenance of the exogenous nucleic acid sequence of interest (insert) inside the transformed cell population. This invention is particularly interesting for fast production of different DNA molecules without antibiotic resistance gene and usable as DNA vaccine or gene therapy for humans or animals.

The inventors firstly tested how control plasmids having nucleotide sequences encoding (coding for) poison proteins and corresponding antidotes proteins may affect the viability of a microbial (prokaryote) cell.

Thereafter, the inventors obtained advantageously a method to select recombinant cells transformed (see FIGS. 6 and 7) with:

a genetic construct comprising a nucleic acid sequence 11 of interest (with no recombination event) and which do not comprises the nucleotide sequence 17 encoding the antidote protein 18 to the second poison protein 19;

a genetic construct (plasmid of the invention) (with no recombination event) and which still comprises and express the nucleotide sequences (14 & 17) that encode the first poison protein 15 and the antidote protein 18, but without antibiotic resistance gene active in the host cell;

the plasmid (vector) of the invention having incorporated the nucleic acid sequence 11 of interest (insert, preferably an insert made of a nucleotide sequence 114 encoding one or more polypeptide(s) 115, this sequence 114 being preferably, after the integration under the control of a (eukaryote or prokaryote) promoter 116) without antibiotic resistance gene active in the host cell, but comprising the nucleotide sequence 17 encoding the antidote protein 18 (and having lost the nucleotide sequence 14 encoding the first poison protein 15). As the following example will clearly demonstrate, these recombinant cells having incorporated correctly (i.e. present inside or having replaced the nucleotide sequence 14 encoding for the first poison protein 15) the nucleic acid sequence 11 of interest (insert) are the only one to survive.

EXAMPLE

The inventors selected an *Escherichia coli* cell having stably incorporated a nucleotide sequence encoding Kis antidote protein.

Figure 6:
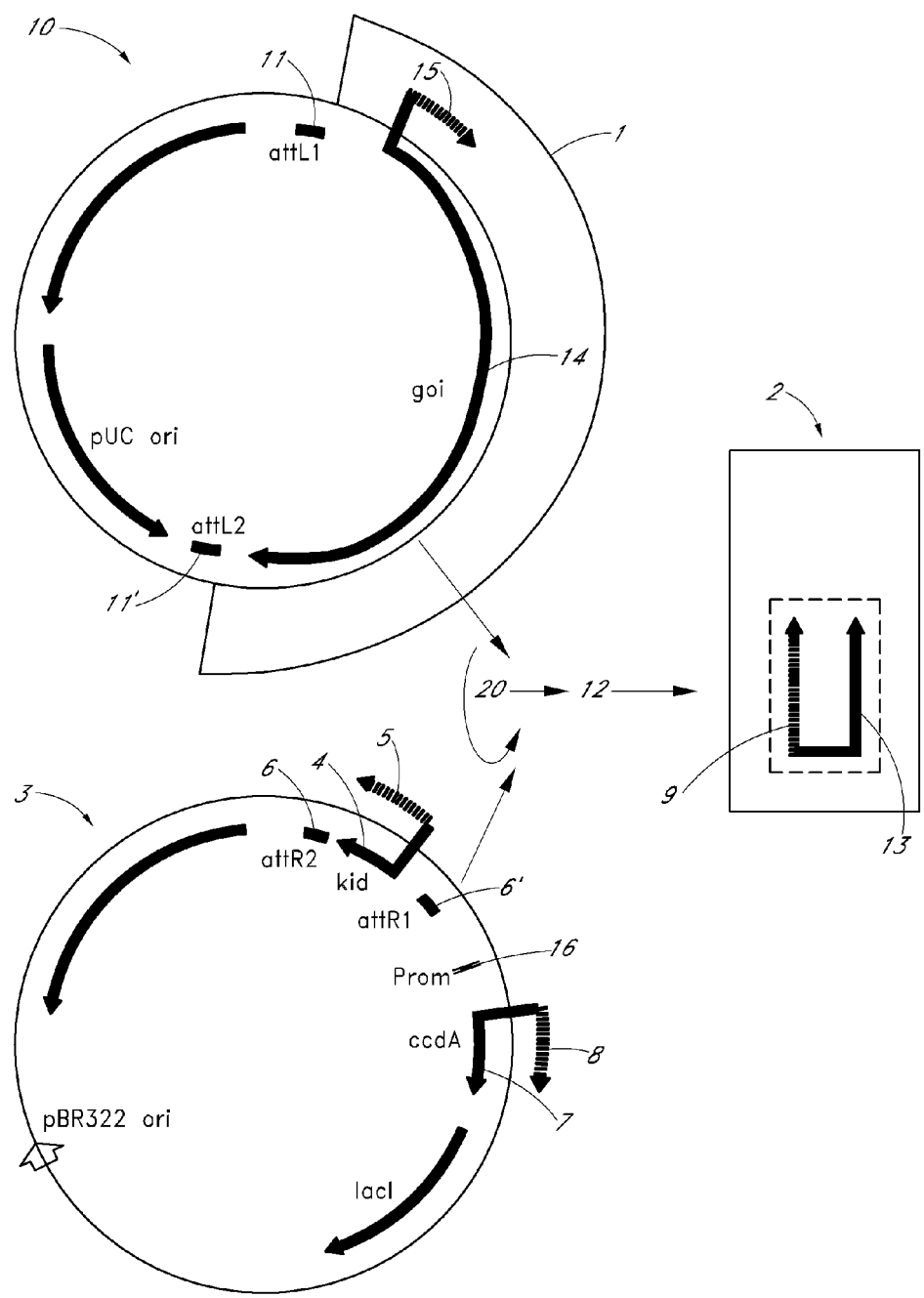
FIG. 6 presents an example of a donor plasmid 110 comprising a nucleotide sequence of interest 11 flanked by recombination sites (111, 111') and a receiving plasmid 13 (pKid-CcdA) with a first nucleotide sequence 14 coding for a first poison protein (Kid=15) under the control of a promoter and flanked by recombination sites (16, 16'), and with a second nucleotide sequence 17 coding for an antidote protein (CcdA=18) to another second poison protein (CcdB=19) different from the first poison protein 15. These two plasmids 110 and 13 by the addition of a recombinase 120 will form a chimeric molecule 112 that is added to an *E. Coli* cell 12, comprising integrated in its genome a nucleotide sequence 113 encoding the poison protein CcdB 19.
Figure 7:
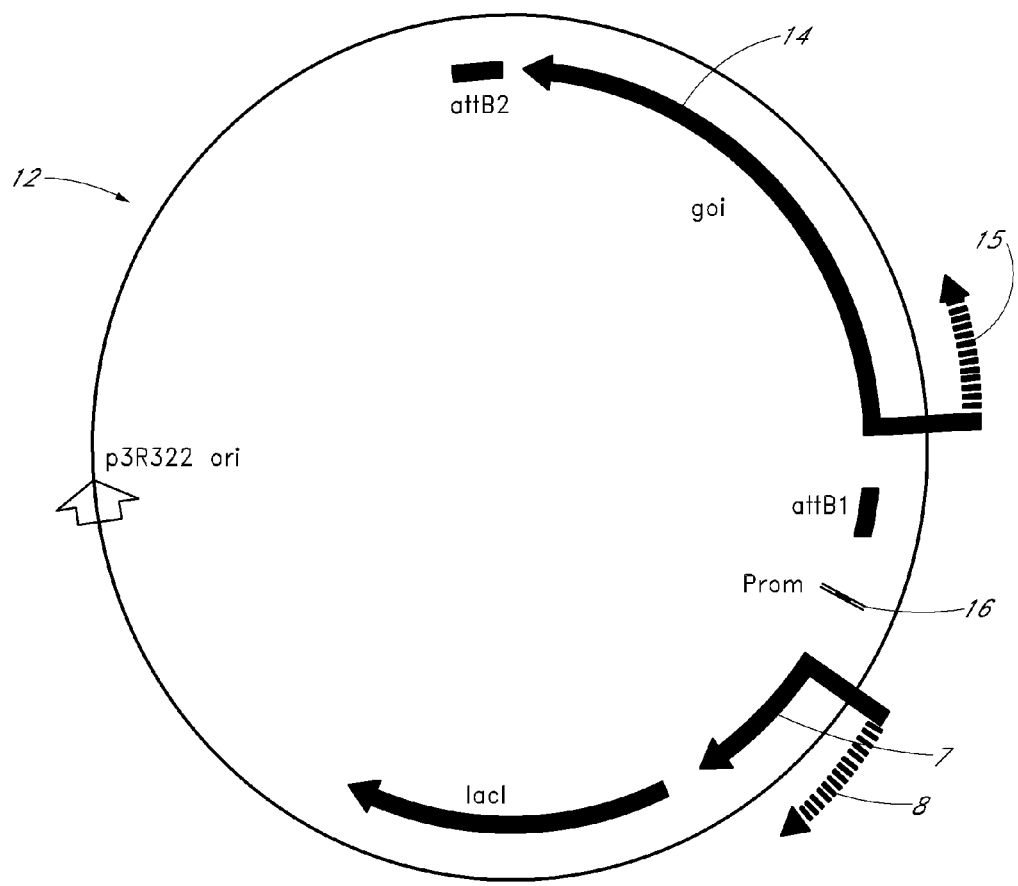
FIG. 7 presents a chimeric molecule 112 corresponding to the receiving plasmid 13 after recombination with the nucleic acid sequence of interest 11, wherein the first nucleotide sequence 14 coding for the first poison protein 15 is removed and replaced by the nucleic acid sequence of interest 11, while the second nucleotide sequence 17 coding for the antidote protein 18 (antidote protein to the second poison protein 19) is used to select the chimeric molecule into the cell 12.

The inventors transformed this *E. coli* cell encoding Kis antidote protein with the plasmid (vector) of FIG. 6 (encoding Kid poison protein, pKidCcdA), to obtain large amounts of this plasmid (acceptor vector). Alternatively, the inventors transformed wild-type *E. Coli* cells with a plasmid (vector) encoding the Kid poison protein wherein the promoter for the expression of Kid poison protein is a regulable promoter and is turned off, to obtain large amounts of this plasmid (vector).

The inventors then added kanamycin resistance gene to the pKidCcdA receiving plasmid (vector, FIG. 6) encoding Kid poison protein and amplified it in the *E. coli* cell encoding the Kis antidote protein. Then, the new plasmid pKidCcdA-Kan was mixed with a genetic construct comprising the nucleic acid sequence 1 of interest (in the form of another plasmid (vector)) flanked by a pair of two different recombination arms (sites) compatible with the pair of two corresponding recombination arms (sites) of the receiving plasmid (vector) and added specific recombinase enzymes in appropriate buffer.

Then the inventors transformed the mixture of plasmids (vectors) into another strain of *E. Coli* 2 encoding CcdB poison protein (CYS21 sold by DelphiGenetics), under the control of the promoter of the ccdA-B operon.

The inventors separated these *E. coli* in two equivalent parts. One part of the bacteria was plated on medium without antibiotics (LB medium) and the other part was plated on medium containing kanamycin (LB medium supplemented with at least 50 μg/ml of kanamycin).

The inventors observed that the amount of colonies was the same on both plates. They analyzed (restriction analysis and sequencing) the surviving cells and observed in both kinds of plates that all cells have been transformed by the receiving plasmids having incorporated the nucleic acid sequence 11 of interest at the position of nucleotide sequence 14 encoding the poison protein 15 (kid gene).

The inventors did not find neither cells without plasmids, neither plasmids comprising nucleotide sequences 14 encoding poison protein 15 (i.e. kid gene even no trace of mutated, non-functional kid), and did not find plasmids wherein the nucleotide sequence encoding the antidote 18 (ccdA) was missing or wherein the nucleic acid sequence 11 of interest was not put in the place of the nucleotide sequence 14 encoding the poison protein 15 (kid).

The inventors repeated the same experiment with the receiving plasmid pKidCcdA without kanamycin resistance gene and observed the same results: same amount of colonies and all colonies with nucleic acid sequence 11 of interest replacing nucleotide sequence 14 encoding the poison protein 15.

The inventors conclude that they can replace antibiotic resistance genes by antidote gene without loss of efficacy in selection during recombination events. The method they developed is easy to carry out, is antibiotics-free and is very efficient in avoiding unwanted clones.

The inventors then monitor the behavior of these transformed cells over time and conclude that the plasmid is efficiently kept under the selection pressure of CcdB (expression of the second poison protein 19 when the plasmid is lost by a bacterium).

To improve the system, the inventors duplicated the poison protein sequences kid, to avoid the counter selection by mutation of recombinant clones, while keeping means (recombination sites) to inactivate both nucleotide sequences.

What is claimed is:

1. A method for sub-cloning and stabilizing a nucleic acid sequence of interest into a cell this method comprising the steps of:
   a) preparing DNA of a receiving vector comprising:
      a first nucleotide sequence encoding a first poison protein;
      a first pair of two different recombination or restriction sites or recombination arms disposed upstream and downstream the said first nucleotide sequence; and
      a second nucleotide sequence encoding an antidote protein to a second poison protein that is different from the said first poison protein, wherein the first and second poison proteins are selected from the group consisting of CcdB, Kid, Doc, RelE, PasA, MazE, and ParE and the antidote protein is selected from the group consisting of CcdA, Kis, Phd, RelB, PasB, PasC, MazF, and ParD;
   b) performing recombination between the said receiving vector and a donor vector, said donor vector comprising the nucleic acid sequence of interest being located between a second pair of two different recombination or restriction sites or recombination arms wherein, this second pair of recombination or restriction sites or recombination arms being compatible with the first pair of two recombination sites or recombination arms of the receiving vector;
   c) obtaining a chimeric nucleic acid molecule comprising the nucleic acid sequence of interest;
   d) transforming the obtained recombination mixture in cell(s) carrying a nucleotide sequence encoding the second poison protein;
   e) obtaining a synthesis of the first poison protein and second poison protein and of the antidote protein to the said second poison protein in the cells;
   f) selecting cells surviving to the toxic activity of the first poison protein and the second poison protein; and
   g) growing and collecting recovered surviving cells comprising the nucleic acid sequence of interest, under selective pressure of the second poison protein.

2. The method according to the claim 1, wherein the second nucleotide sequence is a sequence encoding the CcdA antidote protein to the CcdB poison protein.

3. The method according to the claim 1, wherein the first nucleotide sequence is the sequence encoding the Kid poison protein.

4. The method according to claim 1, wherein the two different recombination sites or arms do not recombine with each other.

5. The method according to claim 1, wherein the step of inserting the nucleic acid of interest is obtained by incubating a mixture mode of the receiving vector and the donor vector, under conditions sufficient to cause recombination between the recombination sites or recombination arms of the first pair and the second pair, thereby producing the chimeric nucleic acid molecule comprising the nucleic acid sequence of interest.

6. The method of claim 1, wherein the step of obtaining the cell is a selection of a cell comprising the chimeric nucleic acid molecule and a selection against a cell comprising the receiving vector or against a cell comprising the donor vector or co-integrate of the donor vector and the receiving vector.

7. The method according to claim 1, wherein the selection of the cell containing chimeric nucleic acid molecule is performed without the addition of antibiotics to the culture medium.

8. The method according to claim 1, wherein the step of inserting the nucleic acid sequence of interest is performed by deletion in the receiving vector of the nucleotide sequence encoding the first poison protein and by its replacement with the nucleic acid sequence of interest.

9. The method according to claim 1, wherein the cell is an *E. Coli* cell.

10. The method of claim 5, wherein the vectors incubation is made in presence of a recombination protein.

11. The method of claim 10, wherein the recombination protein is a recombinase.

12. The method of claim 1, wherein the cell carries the nucleotide encoding the second protein poison in its chromosome.

* * * * *